(12) United States Patent
Akers, Jr.

(10) Patent No.: US 8,871,521 B2
(45) Date of Patent: Oct. 28, 2014

(54) BREATH KETONE DETECTOR

(75) Inventor: Raymond F. Akers, Jr., Sewell, NJ (US)

(73) Assignee: Akers Biosciences, Inc., Thorofare, NJ (US)

( * ) Notice: Subject to any disclaimer, the term of this patent is extended or adjusted under 35 U.S.C. 154(b) by 0 days.

(21) Appl. No.: 13/415,624

(22) Filed: Mar. 8, 2012

(65) Prior Publication Data

US 2012/0231548 A1 Sep. 13, 2012

Related U.S. Application Data

(60) Provisional application No. 61/450,396, filed on Mar. 8, 2011.

(51) Int. Cl.
| | |
|---|---|
| G01N 31/22 | (2006.01) |
| G01N 21/78 | (2006.01) |
| G01N 33/64 | (2006.01) |
| G01N 33/52 | (2006.01) |
| G01N 33/68 | (2006.01) |
| G01N 33/18 | (2006.01) |

(52) U.S. Cl.
CPC ............ *G01N 33/52* (2013.01); *G01N 33/6893* (2013.01); *G01N 33/18* (2013.01); *B01L 2200/16* (2013.01); *G01N 2800/18* (2013.01); *G01N 2800/02* (2013.01); *B01L 2300/0835* (2013.01); *B01L 2300/0832* (2013.01); *G01N 33/1826* (2013.01)
USPC .............. 436/128; 436/127; 422/430; 422/50

(58) Field of Classification Search
CPC ....... G01N 31/22; G01N 33/64; G01N 33/52; G01N 33/493; G01N 21/78
USPC .............................. 436/128, 127; 422/430, 50
See application file for complete search history.

(56) References Cited

U.S. PATENT DOCUMENTS

| | | | |
|---|---|---|---|
| 2,362,478 A | 11/1944 | Galat | |
| 2,509,140 A | 5/1950 | Free | |
| 2,577,978 A | 12/1951 | Nicholls et al. | |
| 3,055,758 A | 9/1962 | McDonald | |
| 4,970,172 A | 11/1990 | Kundu | |
| 6,479,019 B1 * | 11/2002 | Goldstein et al. | 422/84 |
| 7,285,246 B1 | 10/2007 | Martin | |
| 7,837,936 B1 | 11/2010 | Martin | |
| 2003/0208133 A1 | 11/2003 | Mault | |
| 2005/0084921 A1 | 4/2005 | Cranley et al. | |

OTHER PUBLICATIONS

Anderson et al., "Measuring airway exchange of endogenous acetone using a single-exhalation breathing maneuver" J Appl Physiol 100: 880-889, 2006.
Int'l Search Report and Written Opinion issued Jul. 19, 2012 in Int'l Application No. PCT/US2012/028313.
Int'l Preliminary Report on Patentability issued Sep. 19, 2013 in Int'l Application No. PCT/US2012/028313.

* cited by examiner

*Primary Examiner* — Christine T Mui
(74) *Attorney, Agent, or Firm* — Panitch Schwarze Belisario & Nadel LLP

(57) ABSTRACT

Ketoacidosis is an extreme and uncontrolled form of ketosis, which is a normal response to prolonged fasting. Embodiments of this invention test the ketone level of a patient by measuring the ketone bodies in breath condensation. Some embodiments include a device for medical testing comprising a hollow container, comprising powder mixture of sodium nitroferricyanide, ammonium sulfate and silica and a liquid including an ammonium hydroxide solution.

16 Claims, 2 Drawing Sheets

BREATH KETONE DETECTOR

CROSS REFERENCE

This application claims priority to U.S. Provisional Application No. 61/450,396 filed Mar. 8, 2011, which is hereby incorporated by reference in its entirety.

FIELD OF THE INVENTION

This invention relates to devices for the detection of ketone bodies as an aid in the detection and prevention of ketoacidosis.

BACKGROUND

Diabetic ketoacidosis is a serious, potentially life threatening condition. Diabetics are susceptible to this condition, and are often required to be monitored for its presence. Diabetic ketoacidosis is characterized by the accumulation of "ketone bodies" in the blood. These compounds, such as β-Hydroxybutyrate, are byproducts of diabetic metabolism. As ketone bodies accumulate in the blood, they cause a downward shift in the pH of the blood. While prompt treatment for diabetic ketoacidosis is usually successful, failure to treat it can result in serious illness or even death.

Persons with diabetes are typically monitored for the presence of ketone bodies by taking a small blood sample and running an assay for ketone bodies in the blood. Obtaining blood samples is uncomfortable for patients, especially when done frequently as part of a regular monitoring program. The disposal of blood samples presents significant difficulties. Also, the expense of maintaining a device for performing assays on the blood sample, and keeping it at the ready, are significant barriers to compliance with a monitoring program. Often the testing devices are expensive and/or cumbersome.

BRIEF SUMMARY OF THE INVENTION

Embodiments of this invention are described throughout the specification and are not limited to this brief summary.

In certain embodiments, the breath ketone detector is a device for medical testing including a hollow container. In some embodiments, the hollow container includes the reagents. In other embodiments, the hollow container includes a powder and a liquid. In still other embodiments, the powder includes a powder reagent selected from the group consisting of sodium nitroferricyanide, dinitrophenylhydrazine, copper sulfate/potassium sodium tartrate, and combinations of any thereof. In other embodiments, the hollow container further includes a liquid reagent solution.

Certain embodiments of this disclosure include a method for testing for the presence of ketones in breath of a patient. Some embodiments include exposing a powder to the breath of the patient, wherein the powder comprises a powder reagent selected from the group consisting of sodium nitroferricyanide, dinitrophenylhydrazine, copper sulfate/potassium sodium tartrate, and combinations of any thereof. Further embodiments include contacting the powder with a liquid reagent solution to form a combined solution. Still further embodiments include evaluating the color of the combined solution.

DETAILED DESCRIPTION

Figure 1:
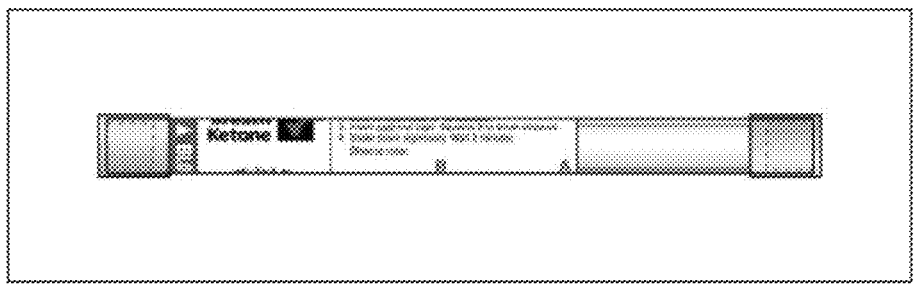
FIG. 1 shows an embodiment of the breath ketone detector with a label and end caps; the ampoules inside the detector are not visible.

Numbers in the present disclosure are rounded to the nearest significant figure using conventional rounding techniques. Ranges of numbers contained herein are understood to contain the numbers on the upper and lower limits, unless otherwise indicated. For instance, a range "from 1 to 10" is understood to include a range including the number "1," and up to and including the number "10." Each number is understood to be modified with the word "about."

The present invention may be embodied in other specific forms without departing from its essential characteristics. The described embodiments are to be considered in all respects only as illustrative and not as restrictive.

The breath ketone detector is a disposable breath ketone detector indicator designed for one-time use. The breath ketone detector contains indicator chemistry that will undergo a color change in the presence of ketone bodies (hereinafter "ketones") contained in the breath of the subject.

The breath ketone detector detects the presence of ketones in a breath condensate sample, which are indicative of blood ketone levels. The breath ketone detector may replace the need for periodic blood or urine ketoacidosis screenings since blood and breath condensate levels of ketones are correlated. Moreover, since ketones are present in the blood before they can be detected in urine, breath ketone detector is designed to identify the presence of ketones at the earliest stages, to facilitate intervention and treatment.

The breath ketone detector is easy to use because it is a compact unit and requires no special instrumentation. The results of the detector are easy to interpret, allowing immediate testing by medical professionals or patients themselves. The breath ketone detector is fast, in some embodiments taking only three steps, requiring approximately three minutes. This qualitative test system enables real-time assessment of a patient's ketone level status.

The breath ketone detector permits rapid identification of medical conditions through biomarkers in breath condensate. In some embodiments, the detector is packaged in a small tube through which the patient can easily blow for several seconds. In certain embodiments, the reactive ingredients are packaged in an ampoule, which is crushed immediately prior to use, releasing the reactive ingredients. Through a catalyzed process, these reactive ingredients form a complex with the biomarker in the breath condensate that is easily viewed as a color change.

One embodiment of the invention includes three components: A) breath ketone detector and end caps, B) the Powder Reagent and, C) the Liquid Reagent. In certain embodiments, the detector consists of two ampoules, one containing the powder reagent and the other containing the liquid reagent. The ampoules are held within the detector tube using plugs. End caps are used to contain the reagent after the ampoules are broken.

The Container

In certain embodiments, the breath ketone detector is a device for medical testing including a hollow container. In some embodiments, the hollow container includes the reagents. In other embodiments, the hollow container includes a powder and a liquid. In still other embodiments, the powder includes a powder reagent selected from the group consisting of sodium nitroferricyanide, dinitrophenylhydrazine, copper sulfate/potassium sodium tartrate, and combinations of any thereof. In other embodiments, the hollow container further includes a liquid reagent solution.

In certain embodiments, the hollow container is any container suitable to hold the powder and liquid. In other embodiments, the hollow container is any container suitable for a patient to blow into such that the breath of the patient comes in contact with the powder. In further embodiments, the hollow container allows the liquid and powder reagents to come in contact with each other.

In one embodiment, the hollow container is a tube. As used herein, tube means a hollow elongated structure. In some embodiments, the tube is cylindrical, or has a circular profile. In other embodiments, the profile of the tube may be a polygon or other shape. In other embodiments, the hollow container is another shape that allows the patient to blow into the hollow container so that the patient's breath contacts the powder. In certain embodiments, the hollow container may be porous, for example, a filter medium, wherein the reagents are distributed on the structure of the filter medium or contained within powder and liquid containers within the hollow container.

In certain embodiments, the powder is contained in a powder container within the hollow container. In some embodiments, the powder container may be breakable or breachable such that the breath of the patient may contact the powder. In other embodiments, the powder container includes openings or pores that allow the breath of the patient to contact the powder through the powder container, and also allows the liquid to contact the powder. In some embodiments, the powder container is a glass ampoule that may be broken within the hollow container. In some embodiments, the glass ampoule may be broken by squeezing a portion of the hollow container adjacent to the glass ampoule.

In certain embodiments, the liquid is contained in a liquid container within the hollow container. In some embodiments, the liquid container may be breakable or breachable such that the liquid may contact the powder. In other embodiments, the liquid container includes openings or pores that allows the liquid to contact the powder. In some embodiments, the liquid container is a glass ampoule that may be broken within the hollow container. In some embodiments, the glass ampoule may be broken by squeezing a portion of the hollow container adjacent to the ampoule.

In some embodiments, the hollow container includes at least one plug inside the hollow container. In certain embodiments, there are plugs located at either end of the hollow container, with the powder container and liquid container located inside the plugs such that the plugs do not allow the powder and liquid containers to exit the hollow container. In some embodiments, the plugs inside the hollow container allow exhaled breath to pass through the tube, but keep the powder inside the tube. In other embodiments, the plug may be made of a permeable or semipermeable material, or may comprise a valve such as a check valve (one-way valve).

In some embodiments, the hollow container includes caps to block any openings in the hollow container. In certain embodiments, the caps may fit over the openings of the hollow container. In other embodiments, the caps may fit inside of the openings of the hollow container. In further embodiments, the caps are removable, in some embodiments, the end caps are not permeable by the liquid from the liquid container. In these embodiments, the caps keep the liquid from the liquid container inside the hollow container after the liquid is released from the liquid container.

Figure 2:
FIG. 2 shows an embodiment of the breath ketone detector with a label and end caps; the ampoules inside the detector are not visible.
Figure 3:
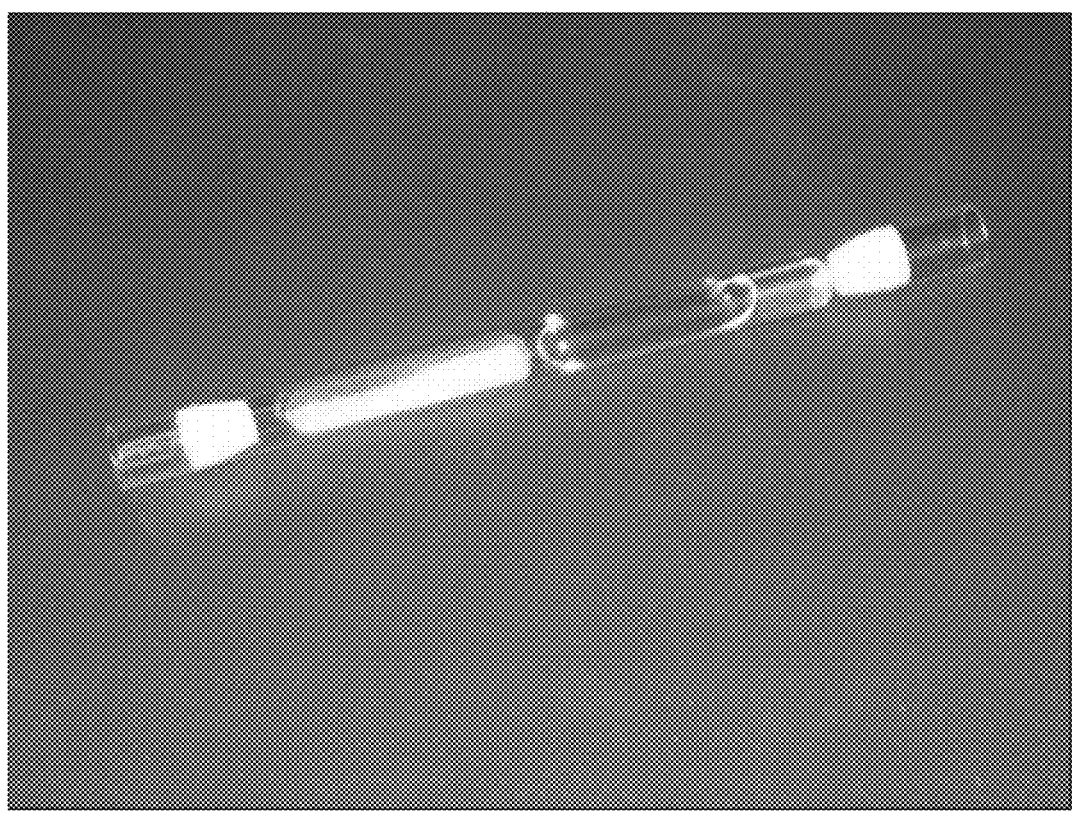
FIG. 3 shows an embodiment of the breath ketone detector without a label or end caps; the powder ampoule, liquid ampoule and plugs inside the tube are clearly visible.

FIGS. 1 and 2 show an embodiment that includes a tube with end caps. The contents of the tube are partially obscured by a label. FIG. 3 shows an embodiment that includes a tube with a powder ampoule, a liquid ampoule and two plugs. This figure does not include end caps or a label.

In one embodiment, the breath ketone detector consists of a PETG detector tube (0.337"×5.0"), polyethylene plugs, rubber end caps, liquid reagent ampoule and powder reagent ampoule.

In certain embodiments, the device does not require any secondary equipment in order to indicate the presence of ketones, for example, gas chromatographs, mass spectrometers, nose clips, rebreathers, flow meters or flow restrictors, or temperature control.

The Powder Component

The breath ketone detector includes at least one powder reagent that is the main component responsible for the color change upon exposure to ketones. In one embodiment, the powder includes a powder reagent selected from the group consisting of sodium nitroferricyanide, dinitrophenylhydrazine, copper sulfate/potassium sodium tartrate, and combinations of any thereof.

In certain embodiments, the powder reagent comprises sodium nitroferricyanide. Sodium nitroferricyanide is also know as sodium nitroprusside, sodium pentacyanonitrosylferrate, SNP, and Sodium pentacyanonitrosylferrate(II). In some embodiments, the powder reagent comprises sodium nitroferricyanide in the amount of 0.36 mg to 36 mg. In other embodiments, the powder reagent comprises sodium nitroferricyanide in the amount of 3.6 mg+/−0.7 mg. In some embodiments, acetone and acetoacetic acid react with sodium nitroprusside in the presence of alkali to produce a purple color. In other embodiments, ammonium sulfate is used to concentrate the ketone bodies to the center of the solution.

In embodiments including copper sulfate/potassium sodium tartrate, the powder reagent may include about 7 mg of copper sulfate (II) and about 35 mg of potassium sodium tartrate. In embodiments including dinitrophenylhydrazine, the powder reagent may include about 100 mg of dinitrophenylhydrazine.

In some embodiments, the powder further comprises a first powder component comprising ammonium sulfate. Ammonium sulfate is also known as: Diammonium sulfate, Sulfuric acid diammonium salt, Mascagnite, Actamaster, Dolamin, Diazanium sulfate. In further embodiments, the first powder component comprises ammonium sulfate in the amount of 9.64 mg to 964 mg. In other embodiments, the first powder component comprises ammonium sulfite in the amount of about 96.4 mg+/−19.3 mg.

In some embodiments, the powder reagent is sodium nitroferricyanide, and the first powder component is ammonium sulfate. In other embodiments, the powder comprises ammonium sulfate in a ratio of nitroferricyanide to ammonium sulfate ranging from about 1:15 to 1:35. In other embodiments, the ratio is about 1:26.7.

In certain embodiments, the powder further comprises a second powder component selected from the group consisting of sodium silicate, calcium sulfate, calcium chloride, montmorillonite clay, molecular sieves, phosphorous pentoxide, cellulose, glass beads, Tenax® (poly(2,6-diphenylphenylene oxide) polymer and combinations of any thereof. In other embodiments, the second powder component comprises 20/50 grade silica. In further embodiments, the second powder component comprises 20/50 grade silica in the amount of about 10 mg to 1 g. In still other embodiments, the second powder component comprises 20/50 grade silica in the amount of about 100 mg+/−20 mg.

Some embodiments include a third powder component selected from the group consisting of glycine, lactose, disodium hydrogen phosphate, and combinations of any thereof. In certain embodiments, the third powder component includes glycine. In certain embodiments, the third powder component acts as an enhancer for color formation of the reaction with the liquid. In embodiments including glycine, the powder may include glycine in an amount of about 25 mg+/−25%. In embodiments including lactose, the powder may include lactose in an amount of about 10 mg+/−25%. In embodiments including disodium hydrogen phosphate, the powder may include disodium hydrogen phosphate in an amount of about 40 mg+/−25%.

In some embodiments, the breath ketone detector powder reagent formulation consists of a pulverized mixture of sodium nitroferricyanide and ammonium sulfate, along with 20/50 grade silica. In certain embodiments, the 20/50 grade silica allows for the entrapment of the volatile ketones captured from breath.

The Liquid Component

Certain embodiments of the device include a liquid component. In some embodiments, the purpose of the liquid component is to accelerate the reaction between the ketones and the powder to minimize the time for color development. In certain embodiments, the liquid includes a reagent solution that comprises a strong base. In some embodiments, the strong base is selected from the group consisting of an alkali hydroxide, an alkaline-earth metal hydroxide, and combinations of any thereof. In still further embodiments, the liquid reagent comprises a strong base selected from the group consisting of ammonium hydroxide, lithium hydroxide, sodium hydroxide, potassium hydroxide, rubidium hydroxide, cesium hydroxide, calcium hydroxide, strontium hydroxide, barium hydroxide, and combinations of any thereof.

In some embodiments, the strong base comprises ammonium hydroxide. In other embodiments, the liquid reagent comprises ammonium hydroxide in the amount of about 50 µL to 2000 µL of 15% to 30% aqueous solution. In other embodiments, the liquid reagent comprises ammonium hydroxide in the amount of about 500 uL of about 15% to 30% solution. In still other embodiments, the liquid reagent comprises ammonium hydroxide in the amount of about 21% to 23% solution.

In one embodiment, the liquid component includes Ammonium Hydroxide and Distilled Water.

The Method

Certain embodiments of this disclosure include a method for testing for the presence of ketones in breath of a patient. Some embodiments include exposing a powder to the breath of the patient, wherein the powder comprises a powder reagent selected from the group consisting of sodium nitroferricyanide, dinitrophenylhydrazine, copper sulfate/potassium sodium tartrate, and combinations of any thereof. Further embodiments include contacting the powder with a liquid reagent solution to form a combined solution. Still further embodiments include evaluating the color of the combined solution.

In certain embodiments, the powder is contained in a first ampoule, the liquid reagent solution is contained in a second ampoule, and the first and second ampoules are contained within a hollow container. Some embodiments further comprise breaking the first ampoule before exposing the powder to the breath. In still further embodiments, exposing the powder to the breath comprises the patient blowing into the hollow container. Certain embodiments further comprise breaking the second ampoule before contacting the powder with the liquid reagent solution, And in still further embodiments, evaluating the color of the combined solution comprises comparing the color of the combined solution to at least one reference color. In other embodiments, the color of the combined solution is compared to a plurality of reference colors.

As discussed above, certain embodiments of the device and method do not require any secondary equipment in order to detect the presence of ketones in the breath. In other embodiments, the patient is only required to blow in the tube for about 30 seconds, and is not required to wear a nose clip, use a rebreather, flow meter, flow restrictor, or control the temperature of the breath or device.

FIG. 1 is indicative of one embodiment of the ketone breath detector. The label on the device includes the letters "A" and "B." The following is a summary of the operation of this embodiment of the invention.

Wait 15 minutes after last food or drink. Remove both end caps from the plastic tube, Squeeze "A" on the outer plastic tube between thumb and forefinger to break inner glass ampoule containing a powder reagent and squeeze only once. Do not crush or bend tube, Take a deep breath and blow for 30 seconds through the end of the tube designated by arrow. Blow very hard. Exhale through the tube, Do not inhale. The plugs inside the tube allow exhaled breath to pass through the tube, but keep the powder inside the tube. Tap the detector to distribute crystals evenly to bottom of tube (area with no label).

Securely place caps on each end of the plastic tube. Squeeze "B" on the outer plastic tube between thumb and forefinger to break inner glass ampoule containing the liquid reagent. Squeeze only once. Do not crush or bend tube. Shake tube vigorously for five seconds, Wait two (2) minutes, Identify color change of reagent.

Visualize the color of the reagent. For a positive result the reagent will turn a blue or purple color. This indicates that the breath ketone detector level is 1.4 mg/dl or greater. For a negative result the reagent will turn a light tan or yellow color. This indicates that the breath ketone detector level is below 1.4 mg/dl.

Embodiments of the device can be configured to detect levels of ketones at specific cut-off values, or in a semi-quantitative way by matching the color of the combined solution to a range of colors that correspond to varying amounts of ketones in the breath. In certain embodiments, as the amount of sodium nitroferricyanide goes up, the test can detect lower levels of ketones. In some embodiments, the color change in the device indicates an amount of ketones above or below about 1.4 mg/dl. This number corresponds to the amount of ketones in a volume of breath condensate solution. This value correlates to the blood value at the time the measurement is taken, but the value is not the same as the amount of ketones in the blood. In these embodiments, the powder may include about 3.6 mg of sodium nitroferricyanide and about 96.4 mg of ammonium sulfate.

In other embodiments, the color change in the device indicates an amount of ketones of above or below about 0.7 mg/dl. In these embodiments, the powder may include about 7.6 mg of sodium nitroferricyanide and about 96.4 mg of ammonium sulfate.

In other embodiments, the color change in the device indicates an amount of ketones of above or below about 1 mg/dl.

In certain embodiments, the powder is initially tan in color while the liquid is clear. After the reaction between the powder and the liquid, if the mixture remains tan or yellow, the level of ketones is below the cutoff amount. If the color of the mixture is purple to bluish gray, the amount of ketones is above the cutoff amount.

EXAMPLE 1

One embodiment of the breath ketone detector was produced for testing having the following characteristics:
Cutoff level: 1.4 mg/dL
Reproducibility: 100%
Time to Result: <3 minutes (avg)
Sample Volume: ~1 L human breath Preliminary real-time studies at 18-22-C performed on these breath ketone detector lots strongly supports an expiry date of 6 months at ambient temperature. The detector is stable without refrigeration when shipping via overnight delivery.

Studies were performed to determine the performance of the breath ketone detector compared to gas liquid chromatography using samples originating from field sources. A total of 57 patients were tested using gas liquid chromatography as compared to the breath ketone. Data showed an overall agreement of 100.0%. The cutoff value was at 1.4 mg/dl. The amount of reagents in each device was:

| | |
|---|---|
| Sodium Nitroferricyanide | 3.6 mg ± 0.7 mg |
| Ammonium Sulfate | 96.4 mg ± 19.3 mg |
| 20/50 Grade Silica | 100 mg ± 20.0 mg |
| Ammonium Hydroxide | 500 μl of 22% Solution |

The reproducibility of the breath ketone detector in detecting the presence of ketones at the cutoff was demonstrated by testing 10 aliquots of an aerosolized ketone sample for inter-day evaluation and 10 aliquots for intra-day evaluation. Reproducibility of the breath ketone detector was determined to be 100% in both studies.

EXAMPLE 2

Precision and Accuracy

Precision and accuracy testing was performed using sixty (60) pre-reacted breath ketone detectors with the amount of reagents listed in example 1. The 60 detectors were charged with simulated acetone breath levels including 20 at 0.00 mg/dl, 20 at 60% below the cut-off (0.56 mg/dl) and 20 at 60% above the cut-off (2.24 mg/dl). The cutoff level was 1.4 mg/dl. The performance of these detectors was 100%.

EXAMPLE 3

Interference Studies

Potential interference studies on test results from cigarette smoke, vibration, and temperature studies were conducted using devices with the amount of reagents listed in example 1.
Acceptance criteria:
Blank sample—no positive readings
Samples 60% below the cut-off—no positive readings
Samples 60% above the cut-off—all positive readings (no negative readings)

The breath ketone test met the acceptance criteria without exception.

EXAMPLE 4

Reproducibility

The reproducibility of the breath ketone test in detecting ketones above 1.4 mg/dl was demonstrated by testing 10 samples of 5 specimens for inter-day evaluation and 10 samples for intra-day evaluation using devices with the amount of reagents listed in example 1. Reproducibility of the breath ketone test was determined to be 100% in both studies.

EXAMPLE 5

Field Studies

Eighty (80) human subjects were evaluated by the breath ketone test and the Ketocheck urine dipstick test (Clarity) for ketones. The cutoff value for the breath ketone test was 1.4 mg/dl with the amount of reagents listed in example 1. Fifty (50) normal, healthy subjects produced negative results on both tests. Thirty (30) subjects previously diagnosed with diabetes and under the care of a physician had either a negative or trace result by the Ketocheck method, and twenty-nine (29) of the subjects were negative by the breath ketone test. One of these subjects produced a positive result with the breath ketone test. This subject also had an elevated blood serum level (3× normal range) of the ketone beta-hydroxybutyrate level.

EXAMPLE 6

Clinical Performance Testing

A clinical evaluation of the breath ketone test was performed using fresh samples originating from field sources. The breath ketone test results was compared to a standard Ketone rapid blood test.

The objective of this study was to evaluate the performance of the breath ketone test rapid assay compared to a standard blood testing method using fresh samples originating from field sources to determine if there was a relationship between the two methods. The test was conducted by professionals in a medical facility using a cleared test method. Participants were previously diagnosed with diabetes and under a physician's supervision. Each subject was tested with the breath ketone test and Precision Xtra (Abbott Laboratories) Ketone tests. The Precision Xtra test tests blood from a patient, typically from a finger stick.

A total of 40 subjects were recruited for the study. The blood ketone levels were determined with a finger stick sample. The blood ketone levels of the participants were unknown to the person performing the breath condensate testing, and the breath condensate results were unknown to the person performing the blood ketone testing. Samples were also tested by the breath ketone test and urine dipsticks on site. As necessary, blood samples were sent to a reference laboratory for additional testing. Any discrepant results were followed up by sequentially collecting whole blood in a tube containing EDTA. The whole blood aliquot was sent to a reference laboratory. Any samples which are hemolyzed, lipermic, or contain bacterial contamination were unsuitable for use. Following testing, the aliquot were stored at 4° C., in the case that re-testing was necessary.

Forty (40) human subjects were evaluated by the breath ketone test and the Precision Xtra test for blood ketones. The breath ketone test was positive if the ketone level was greater than 1.4 mg/dl, and negative below this level. The Precision Xtra test was positive if the ketone level was greater than 1.5 mmol/l, and negative below this level. 1.4 mg/dl of ketones in breath corresponds to 1.5 mmol/l of ketones in blood. The Detection Success Rates of the breath ketone test in this study were calculated as follows. The 2×2 contingency table below shows the distribution of all corresponding paired measurement values for the breath ketone test versus the reference method for blood ketone levels (Precision Xtra test) for blood ketones <1.5 mmol/l and ≥1.5 mmol/l. There were 6 samples with a true ≥1.5 mmol/l level and 34 samples with a true <1.5 mmol/11 level. The identity or agreement in this table between the values detected by the breath ketone test and the reference method is along the diagonal from the upper left Quadrant A to the lower right Quadrant D.

|  | A 34 | B 0 |
|---|---|---|
|  | C 0 | D 6 |
| Column Totals: | 34 | 6 |

In quadrant D, there were 6 cases where the reference method indicated a ≥1.5 mmol/l level and the breath ketone test succeeded in detecting that condition. The detection success rate was 100%. In quadrant A, there were 34 cases where the reference method indicated a ketone level<1.5 mmol/l and the breath ketone test succeeded in detecting that condition. A <200 mg/dl detection success rate was 100%. The values of 0 in quadrants B and C indicate that there were no discrepancies between breath ketone test and the reference test.

I claim:

1. A device for medical testing for the presence of ketones in breath of a patient, comprising a hollow container, the hollow container containing:
   a powder comprising
      a powder reagent selected from the group consisting of sodium nitroferricyanide, dinitrophenyihydrazine, copper sulfate/potassium sodium tartrate, and combinations of any thereof; and
      a powder component selected from the group consisting of sodium silicate, calcium sulfate, calcium chloride, montmorillonite clay, molecular sieves, phosphorous pentoxide, silica, cellulose, glass beads, poly(2,6-diphenylphenylene oxide polymer and combinations of any thereof; and
   a liquid reagent solution comprising a strong base selected from the group consisting of an alkali hydroxide, an alkaline-earth metal hydroxide, and a combination of any thereof,
wherein the hollow container is configured such that the breath comes in contact with the powder after the patient blows into the hollow container, and the powder changes color upon exposure to the ketones and the liquid reagent solution.

2. The device of claim 1, wherein the powder further comprises ammonium sulfate.

3. The device of claim 2, wherein the powder further comprises a third powder component selected from the group consisting of glycine, lactose, disodium hydrogen phosphate, and combinations of any thereof.

4. The device of claim 1, wherein the powder comprises sodium nitroferricyanide in an amount of 0.36 mg to 36 mg, 20/50 grade silica in the amount of 10 mg to 1 g, and ammonium sulfate in an amount of 9.64 mg to 964 mg; and the liquid reagent solution comprises ammonium hydroxide in an amount of 50 µL to 2000 µL of 15% to 30% aqueous solution.

5. The device of claim 1, wherein the powder is contained in a first ampoule, the liquid reagent solution is contained in a second ampoule, and the first and second ampoules are contained within the hollow container.

6. A method for testing for presence of ketones in breath of a patient using the device of claim 1, comprising:
   exposing the powder to the breath of the patient;
   contacting the powder with the liquid reagent solution to form a mixture; and
   evaluating color of the mixture.

7. A device for medical testing for the presence of ketones in breath of a patient, comprising a first ampoule and a second ampoule, wherein
   the first and second ampoules are contained within a hollow container;
   the first ampoule contains a powder comprising about 3.6 mg sodium nitroferricyanide, about 100 mg 20/50 grade silica, and about 96.4 mg ammonium sulfate; and
   the second ampoule contains a liquid reagent solution comprising about 500 µL of about 22% ammonium hydroxide aqueous solution,
   wherein the hollow container is configured such that the breath comes in contact with the powder after the patient blows into the hollow container, and the powder changes color upon exposure to the ketones and the liquid reagent solution.

8. A method for testing for presence of ketones in breath of a patient using the device of claim 7, comprising:
   breaking the first ampoule;
   exposing the powder to the breath by the patient blowing into the hollow container;
   breaking the second ampoule;
   contacting the powder with the liquid reagent solution to form a mixture; and
   evaluating the color of the mixture.

9. A method for testing for presence of ketones in breath of a patient, comprising:
   exposing a powder to the breath of the patient by the patient blowing into a hollow container containing the powder, wherein the powder comprises
      a powder reagent selected from the group consisting of sodium nitroferricyanide, dinitrophenylhydrazine, copper sulfate/potassium sodium tartrate, and combinations of any thereof; and
      a powder component selected from the group consisting of sodium silicate, calcium sulfate, calcium chloride, montmorillonite clay, molecular sieves, phosphorous pentoxide, silica, cellulose, glass beads, poly(2,6-diphenylphenylene oxide polymer and combinations of any thereof;
   contacting the powder with a liquid reagent solution to form a mixture, wherein the liquid reagent comprises a strong base selected from the group consisting of an alkali hydroxide, an alkaline-earth metal hydroxide, and a combination of any thereof; and
   evaluating color of the mixture.

10. The method of claim 9, wherein the powder is contained in a first ampoule, the liquid reagent solution is contained in a second ampoule, and wherein the first and second ampoules are contained within a hollow container.

11. The method of claim 10, further comprising:
breaking the first ampoule before exposing the powder to the breath, wherein exposing the powder to the breath comprises the patient blowing into the hollow container; and
breaking the second ampoule before contacting the powder with the liquid reagent solution.

12. The method of claim 9, wherein evaluating color of the mixture comprises comparing the color of the mixture to at least one reference color.

13. The method of claim 9, wherein the powder further comprises ammonium sulfate and silica.

14. The method of claim 13, wherein the powder comprises sodium nitroferricyanide in an amount of 0.36 mg to 36 mg, 20/50 grade silica in an amount of 10 mg to 1 g, and ammonium sulfate in an amount of 9.64 mg to 964 mg; and the liquid reagent solution comprises ammonium hydroxide in an amount of 50 μL to 2000 μL of 15% to 30% aqueous solution.

15. The device of claim 1, wherein the strong base is selected from the group consisting of ammonium hydroxide, lithium hydroxide, sodium hydroxide, potassium hydroxide, rubidium hydroxide, cesium hydroxide, calcium hydroxide, strontium hydroxide, barium hydroxide, and combinations thereof.

16. The method of claim 9, wherein the strong base is selected from the group consisting of ammonium hydroxide, lithium hydroxide, sodium hydroxide, potassium hydroxide, rubidium hydroxide, cesium hydroxide, calcium hydroxide, strontium hydroxide, barium hydroxide, and combinations thereof.

* * * * *